United States Patent
Yancie

(10) Patent No.: US 11,547,612 B2
(45) Date of Patent: Jan. 10, 2023

(54) TRAINING UNDERGARMENT

(71) Applicant: Jennifer Yancie, Southfield, MI (US)

(72) Inventor: Jennifer Yancie, Southfield, MI (US)

(*) Notice: Subject to any disclaimer, the term of this patent is extended or adjusted under 35 U.S.C. 154(b) by 231 days.

(21) Appl. No.: 15/996,252

(22) Filed: Jun. 1, 2018

(65) Prior Publication Data
US 2020/0315862 A1 Oct. 8, 2020

(51) Int. Cl.
*A61F 13/49* (2006.01)
*A41B 9/00* (2006.01)
*A61F 13/56* (2006.01)
*A61F 13/15* (2006.01)
*B32B 27/12* (2006.01)
*B32B 5/26* (2006.01)
*A61F 13/511* (2006.01)

(52) U.S. Cl.
CPC ........ *A61F 13/49004* (2013.01); *A41B 9/001* (2013.01); *A61F 13/49011* (2013.01); *A61F 13/5116* (2013.01); *B32B 5/26* (2013.01); *B32B 27/12* (2013.01); *A41B 2300/324* (2013.01); *A41B 2400/44* (2013.01); *A41B 2400/62* (2013.01); *A41B 2400/70* (2013.01); *A61F 2013/49088* (2013.01); *B32B 2307/7265* (2013.01); *B32B 2437/00* (2013.01); *B32B 2555/02* (2013.01)

(58) Field of Classification Search
CPC .......... A61F 13/49004; A61F 13/49006; A61F 13/49011; A61F 13/5116; A61F 13/15268; A61F 2013/15276; A61F 13/49061
See application file for complete search history.

(56) References Cited

U.S. PATENT DOCUMENTS

| 5,185,011 A | * | 2/1993 | Strasser | A61F 13/49004 |
| | | | | 604/385.15 |
| 2008/0110775 A1 | * | 5/2008 | Beck | A61F 13/505 |
| | | | | 206/229 |
| 2013/0012903 A1 | * | 1/2013 | Labit | A61F 13/493 |
| | | | | 604/378 |

(Continued)

FOREIGN PATENT DOCUMENTS

KR 20160134191 A * 11/2016 ............. A61F 13/53

OTHER PUBLICATIONS

Madizzysmum; Flip Training Pant Review; youtube.com video; https://www.youtube.com/watch?v=A91RAjyq7Nc; accessed Dec. 6, 2021; published Jan. 19, 2012. (Year: 2012).*

*Primary Examiner* — Daniel J Colilla

(57) ABSTRACT

An undergarment facilitating the process to transition from disposable protective undergarments and diapers to underwear or "toilet/potty-training" in individuals where a subject is able to access and use facilities independently and at the proper time. The training undergarment can be made of textile of differing colors and prints with a particular thickness integrated with fasteners, which lock together creating a garment with a front and back. The snaps enable the training undergarment to be removed by unsnapping the closures and removing said undergarment without the individual becoming completely undressed or disrobed. The training undergarment protects the clothing of the individual from excrement in said transition until the individual is fully "trained" and able to use proper facilities at the proper time.

5 Claims, 6 Drawing Sheets

(56) References Cited

U.S. PATENT DOCUMENTS

| | | | |
|---|---|---|---|
| 2014/0257230 A1* | 9/2014 | Wang | A61F 13/5644 604/394 |
| 2016/0058631 A1* | 3/2016 | Ormsby | A61F 13/622 604/391 |
| 2018/0193205 A1* | 7/2018 | Beck | A61F 13/15211 |
| 2020/0163810 A1* | 5/2020 | Johnson | A61F 13/49011 |
| 2020/0163812 A1* | 5/2020 | Zuleger | A61F 13/49011 |
| 2021/0030602 A1* | 2/2021 | Kreuzer | A61F 13/494 |

* cited by examiner

TRAINING UNDERGARMENT

CROSS REFERENCE TO RELATED APPLICATIONS

This application claims the benefit of U.S. Provisional Application No. 62/501,272 filed on May 4, 2017 which is incorporated by reference in its entirety.

FIELD OF INVENTION

The field of invention is potty-training products (pull-on diapers, trainers, plastic pants, etc.) and accidental human excrement soil prevention of clothing with absorbent tools (diapers, pads and diaper-like products) for personal wear. Solutions for children learning to control their bladder and becoming potty-trained as well as adults looking for a discrete solution for incontinence for whatever reason are numerous but rarely effective. A number of training options exist but tend to be hazardous and toxic to the subject-wearer, dangerous environmentally (disposable), difficult to incorporate discretely (diapers), costly, not as durable and generally not as effective for all ages and sexes.

BACKGROUND OF INVENTION

The present invention was created after using all options on the market for "potty-training" and incontinence challenges and finding those options to be unacceptable for several reasons. Some of the reasons include being inept at aiding in training the subject to actually go to the bathroom by being: too absorbent, too focused on shielding wetness, too cheaply constructed, too costly, too toxic, and too environmentally unsafe. The unacceptable attributes are largely because the training products consist largely of diapers and diaper-like products. The early introduction of potty-training and incontinence tools have largely focused on being absorbent.

Notwithstanding absorbency, the next generation of tools focused on being convenient and the garments being disposable. Hence, the use of cheap and toxic fillers and liners in diapers and diaper-like products began to be commonplace. The most recent innovation in current art includes all of the aforementioned attributes plus the use of graphics and tactile sensation to aid the subject-wearer in becoming oriented to using the available facilities instead of the garment. The graphics are to help the child and caregiver understand the garment is soiled in some way. The tactile reaction is a sensation sent to the subject-wearer from the garment to alert of the garment being soiled. Newer art further focuses on more convenience with the inclusion of seams attached by fasteners which can be opened and closed at-will. However, the designs have not been durable, discreet or secure for the user.

All children will go through the potty-training process at some age. For some children, it is quick and painless. For other children and sometimes adults, it is not so easy. Some of the challenges faced in the process are due in large part to the current tools on the market. The principal improvement with the training undergarment disclosed herein is its protective make-up which allows for an absorbent nature while still allowing the subject-wearer to feel wetness but also still preserving their clothing and their environment from wetness.

The present invention is designed to eliminate the issues and challenges with products currently on the market and in production. The disclosed invention herein is: non-toxic, environmentally-friendly, reusable, cost-efficient, washable, durable, simple to use, effective, not overly absorbent, more like underwear than a diaper, superior in aiding early childhood development and can help children of all ages facing challenges in potty-training as well as adults facing the challenges of incontinence and is good for both females and males.

A large part of the challenge in potty-training is alerting the subject to go to the bathroom when the urge to urinate or defecate arises. This urge, when supplemented by wet or soiled garments, should lead the subject to become uncomfortable and over time, essentially resulting in the subject using the facilities instead of the training garment. If a garment is too absorbent, the subject will not become as uncomfortable as necessary to lead to the subject's resolution from or prevention of soiling the garment. The importance of the urge is reduced because of the high level of absorbency of the garment leads masks feeling of wetness which then reduces the priority of using the facilities and ultimately ignoring the urge. This impedes the rate at which a subject "takes" to being trained to relieve him or herself in the facilities rather than in the "trainer." Not feeling the wetness allows the subject-wearer to ignore the urge because he/she is protected from the result—a soiled garment. The level of absorbency can keep the subject-wearer from an urgency to stop using the garment for excrement and even the urge to remove the garment because he/she cannot feel the discomfort. The invention disclosed herein answers this challenge.

Because many parents and caregivers struggle with potty-training and managing incontinence in children of all ages and even adults, another way this invention will help with the overall training process and the management of incontinence is by providing an efficient, effective and inexpensive garment. The invention disclosed herein is an easier and cheaper alternative to the current solutions being marketed i.e. diapers, pads, and disposable underwear, and in its preferred embodiment it feels rather luxurious and rich because of the textile used in the construction. Adding the current invention into the training regimen can save nearly $1500 for the patent or caregiver using pull-on disposable trainers and other diaper-like supplies currently on the market. The toxic nature of cheap products on the market is a real concern for parents and caregivers when using for babies, children and other classes of subject-wearers. The toxicity causes skin irritation and rashes. The present invention, the training undergarment, can also be re-used until the subject outgrows the garment or becomes proficient and is potty-trained, saving the parent or caregiver time and money. The idea is the design and mechanism by which the present invention facilitates training will allow subject to become trained faster than currently possible with other trainers on the market. Further, this invention is washable by normal washing methods both by hand or by machine. Parents and caregivers are saved from purchasing diaper-like trainers over and over again throughout the "potty-training" process which can last for months or even years.

The latest options in potty-training innovation include graphics and sensations upon wetness or soiling. While this is helpful for the parent or caregiver for alerting the subject has soiled themselves, the practicality of these notions can backfire as "rewards" for soiling the garment. The graphics show up on the diaper-like trainer or garment once it is soiled. Perhaps this was a great idea in theory but in practice when things appear, especially to children, it is more of a game or magic trick. A magic trick which can only be brought about by the subject soiling the garment with no prompting towards using the facilities. Perhaps a negative reaction in the trainer would be more purpose-driven for the trainer. If the subject uses the garment and soils it, the picture should disappear. This "nothing" to "something" would appeal to most subject-users for the purpose intended; besides alerting their parents or caregivers of a soiled garment, as a reward and not a negative result. This effect would not further the purpose intended.

As for the tactile sensations given to the subject by the garment upon soiling; this would also seem to be counter the goal of deterring the behavior of soiling the garment. Not being able to dispense anything more than a slight vibration or tingle, effectiveness seems questionable. The tactile sensation is to reduce garment soiling and induce the subject to use the facilities. The subject can, again, view a slight sensation by the garment as a reward prompting the subject to actually avoid going to the facilities to release to feel the sensation. However, any stronger of a sensation which would actually prompt the child in a manner to go to the toilet instead of soiling the garment would quite possibly be inhumane. Both the graphics and the sensations as tools to aid garments in deterring subjects from soiling their training garments seem to miss the effective mark and can arguably counter potty-training efforts altogether. The effects of these products could actually lead to stretching the training process out for a lot longer than needed.

Another challenge with current art is the inclusion of padding, both fixed and non-fixed padding, which can move around and leave clothing susceptible to excrement and waste. Padding in and of itself tends to not be reusable contributing to waste; it also has to be purchased throughout the training process making it cost prohibitive; further, it can be uncomfortable because it can bunch up in odd places for the subject-wearer; and finally, it is sometimes removable which means it is not stationary and misses the mark on protecting in the manner intended and causing un-planned friction while subject-wearer is moving often preventing the sensations needed for the appropriate sensory responses used in training if at all and preventing learning through embarrassing "accident" situations. The pull-on diaper-like garments used in potty-training tend to have the same issues and thus less effective in the training process.

For as far as the world of trainers has come, the options which include durability, eco-friendly, effective, absorbent-enough, sensory stimulating, underwear-like solutions have just not evolved as quickly. However, the current invention addresses all of these concerns and offer improvements over the aforementioned challenges. The current invention further improves over current art in the look and feel of the trainer combined with how the trainer is easily accessed on subject-wearer.

SUMMARY OF INVENTION

In one aspect of the present disclosure described herein, a training undergarment providing a superior training experience in the look and feel of the garment which includes a durable design, environmentally friendly fabric choice and use, absorbent-enough for sensory stimulation but not too absorbent panel aiding in a faster training process but also protective of clothing and the subject-wearer's environment should an accident happen and with simple access to remove and change the soiled garment which is non-toxic and reusable. The training undergarment disclosed herein also comprises layers of absorbent material co-layered inclusive of a layer impermeable to liquid creating a unique collection of layers comprising the absorbent panel.

The undergarment further consists of an expandable, elastic waistband and two leg openings with slightly elastic bands creating a comfortable fit. The garment also features a front and back panel which are continuous in design, but to support ease of attachment or removal, the panels come together on either lateral side with multiple fasteners in a vertically-oriented layout on the front panel to secure the garment when worn. The front panel connects to the back panel via fasteners around subject-wearer's genitals by way of the fasteners to form and secure the garment for wearing. The absorbent panel is longitudinally placed in the center of the training undergarment and nested in the waistband of the front and back panels. This simple construction has a stationary absorbent panel which, because it does not move provides more protection and stability of the absorbent layer which also alleviates irritating bunching of material in weird or odd places in the garment leading to friction and making subject-wearer uncomfortable. This garment has no padding. The training undergarment is less like its diaper and diaper-like counterparts in the current art and is more equivalent to clothing. It is also fully washable and reusable.

The training undergarment is constructed to not only focus on potty-training, but incontinence in young adults and adults. The disclosure herein is superior in use, construction and material over the current diaper and diaper-like innovations on the market. The design and construction disclosed herein further increases the effectiveness and ease of use for parent's and caregiver's convenience. The construction also fully protects the individual's clothing and surroundings should the subject-wearer soil the training undergarment.

DETAILED DESCRIPTION

Figure 1:
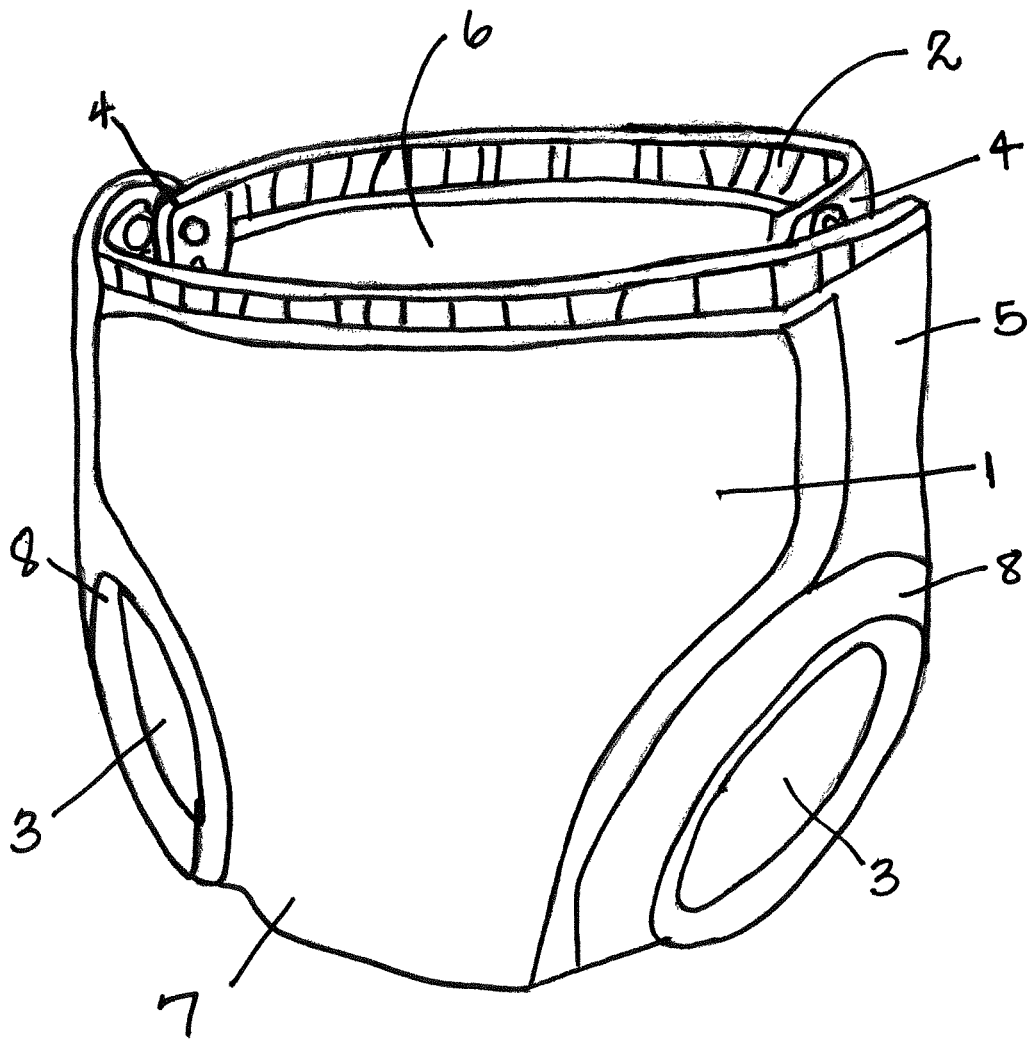
FIG. 1 is a front view of the present invention shown in the form of a training undergarment with two openings for subject-wearer's legs, an elastic waistband, a multi-layer absorbent panel extending down from the waistband, lining the front panel down to the area between the two openings for legs where it continues, unbroken, on through to lining the back panel of the garment ending at the elastic waistband as it began. The fasteners are vertically oriented and placed on either side of the garment laterally-placed in a plurality to secure the garment. The male section of the fasteners attached to outside of the back panel and the female housing for the fasteners on the inside of the front panel are placed one to one to affix the garment securely together for the subject-wearer.

Referring to the drawings now and in particular describing the disclosure described herein as mentioned in the Brief Summary of the present disclosure above-listed and in the claims below, referring to FIG. 1 a training undergarment in its entirety indicated by the reference number 7. The training undergarment 7 which is fully reusable, washable and non-toxic, is not disposable or discarded after one use and is crafted with durability of design to withstand multiple use. The present invention is not to be used with any other absorbent garment and is to be worn with protective outer garments if so desired which is inclusive of the scope of the present invention. The construction of the garment by way of illustration, can be comprised of various materials however the preferred materials are environmentally-friendly, possibly organic and made from a soft textile to deliver a soft tactile feel for subject-wearer.

The training undergarment 7 is illustrated in FIG. 1 in a partially fastened and partially assembled-for-wear condition. The undergarment 7 has a front panel 5 which exhibits the front region of the multi-layer absorbent panel 1 integrated into the front panel and directly adjacent to the leg openings 3 which are laterally placed on either side of the training undergarment 7. Each leg opening 3 is defined by a circularly defined space for the subject-wearer's legs and has an elastic property to mildly adjust to the girth of subject-wearer's thigh size. At the waistband 2 of the undergarment 7 there is a full elastic quality to encircle subject-wearer at the waist and to fully adjust to the size of the subject-wearers waist for comfortability. The front panel 5 houses the fasteners 4 by which the entire undergarment 7 is assembled with the connecting fasteners 4 on the back panel 6. The fasteners 4 are nested into the sides of the front panel 5 and the back panel 6 in a vertical orientation to align the front panel 5 and the back panel 6 when the undergarment 7 is fully assembled. The fasteners 4 are oriented laterally on the undergarment 7 on the upper sides of each of the front panel 5 and the back panel 6 for smooth integration on the subject-wearer to be discreet when fully assembled under clothing.

Figure 2:
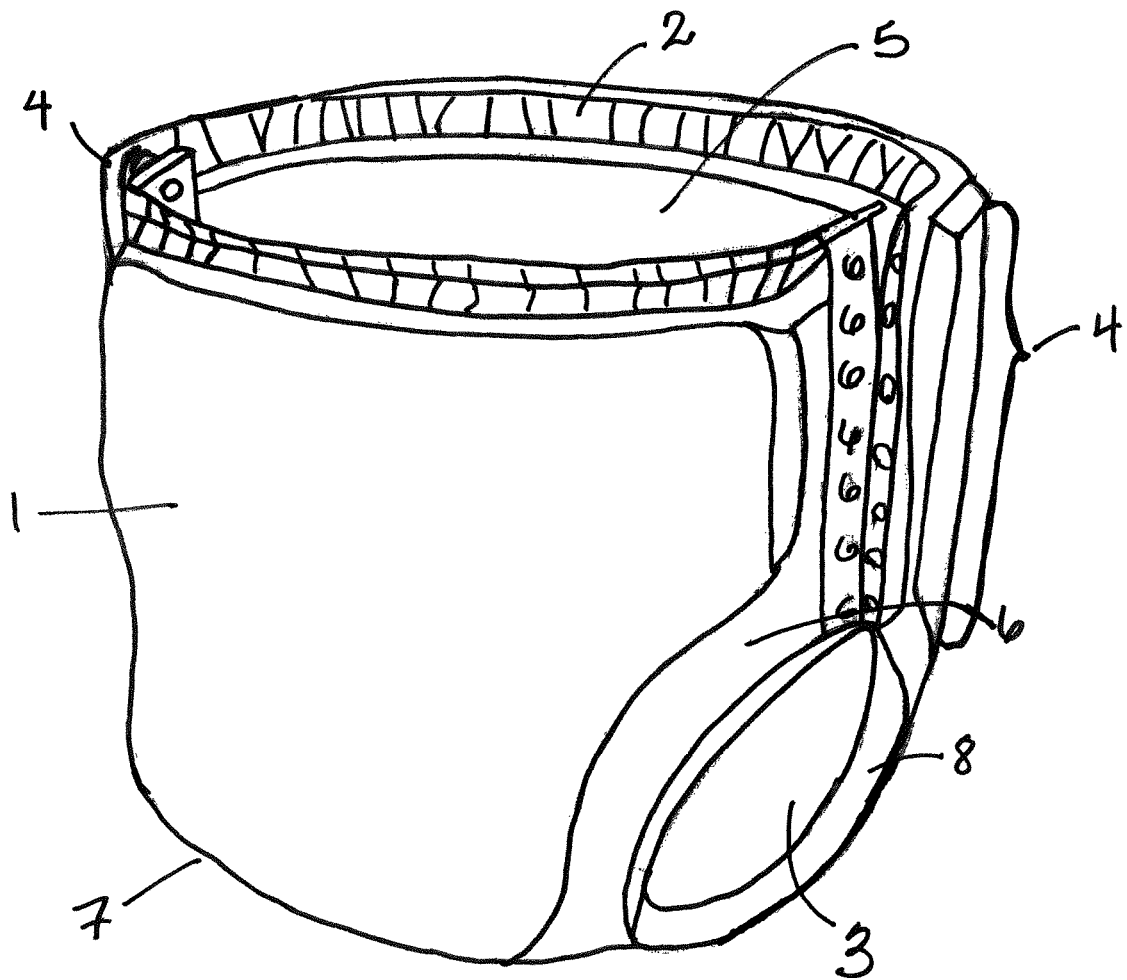
FIG. 2 is a rear view of the present invention shown in the form of the training undergarment with one visible leg opening, the elastic waistband and the multi-layer absorbent panel. The orientation of the fasteners on the present disclosure of the training undergarment are seen from another perspective where the nesting of the front panel and the back panel can be seen from a closer view of the fasteners. The plurality of fasteners is designed to nest smoothly on the garment so as to complete the construction of the training undergarment without excess fabric and bulkiness when worn making present invention discreet.

Referring to the illustrated undergarment 7 in FIG. 2 now, shows a view from the rear of the undergarment 7 not completely assembled but in a configuration of how the undergarment 7 would be assembled, showing a plurality of fasteners and how the alignment of the front panel 5 with the back panel 6 and the fasteners on both panels will create a lateral vertical seam for the undergarment 7 when fastened. Once fastened as demonstrated in FIG. 2, the plurality of fasteners complete closure of the leg openings 4 which then yield a fully assembled undergarment 7. In this illustration of the rear of the undergarment 7, the elastic waistband 2 can be seen further extending around the top of the front panel 5 and the back panel 6 in reference to what is shown in FIG. 1 with a view of a region of the multi-layer absorbent panel integrated into the back panel 6 of the undergarment 7.

Figure 3:
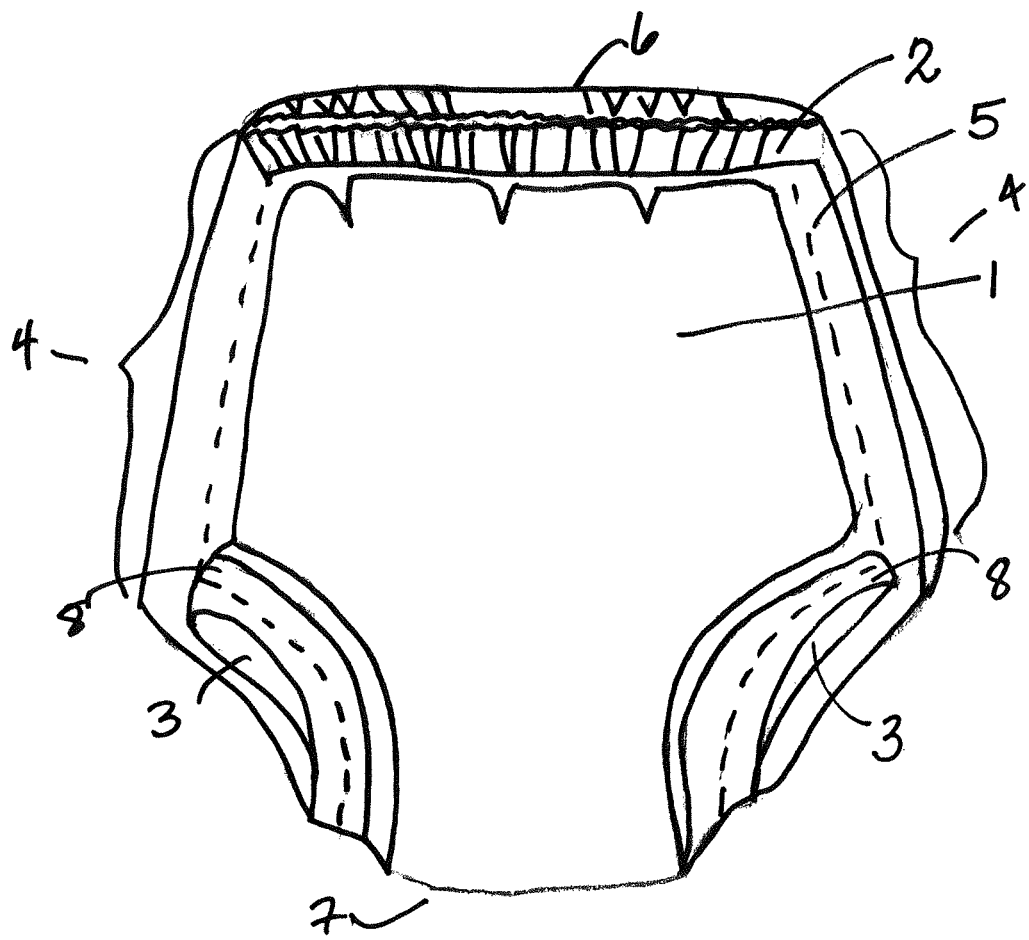
FIG. 3 is the closed front-view of the present invention in the form of the training undergarment with two visible leg openings, the front panel of the garment inclusive of the continuous multi-layer absorbent panel which nests in the front region area of the elastic waistband with the elastic waistband. The fasteners are fully engaged closing the undergarment connecting the front and back panels.

Referring now to the illustration in FIG. 3 is a front closed, fully assembled view of the undergarment 7 as it would look when ready to don the undergarment 7. The leg openings are visible on each lateral side of the front panel 5. The fasteners 4 are fully engaged in this view and therefore completely obscured from the front view as they are when the garment is fully assembled. The elastic waistband 2 encircling the entire undergarment 7 can be seen in this illustration inclusive of the back region of the waistband, which is only partially visible. The lateral leg openings 4 and the seams created by the engaged fasteners give the undergarment 7 the balance in its durable design for optimal effectiveness as a training undergarment 7.

Figure 4:
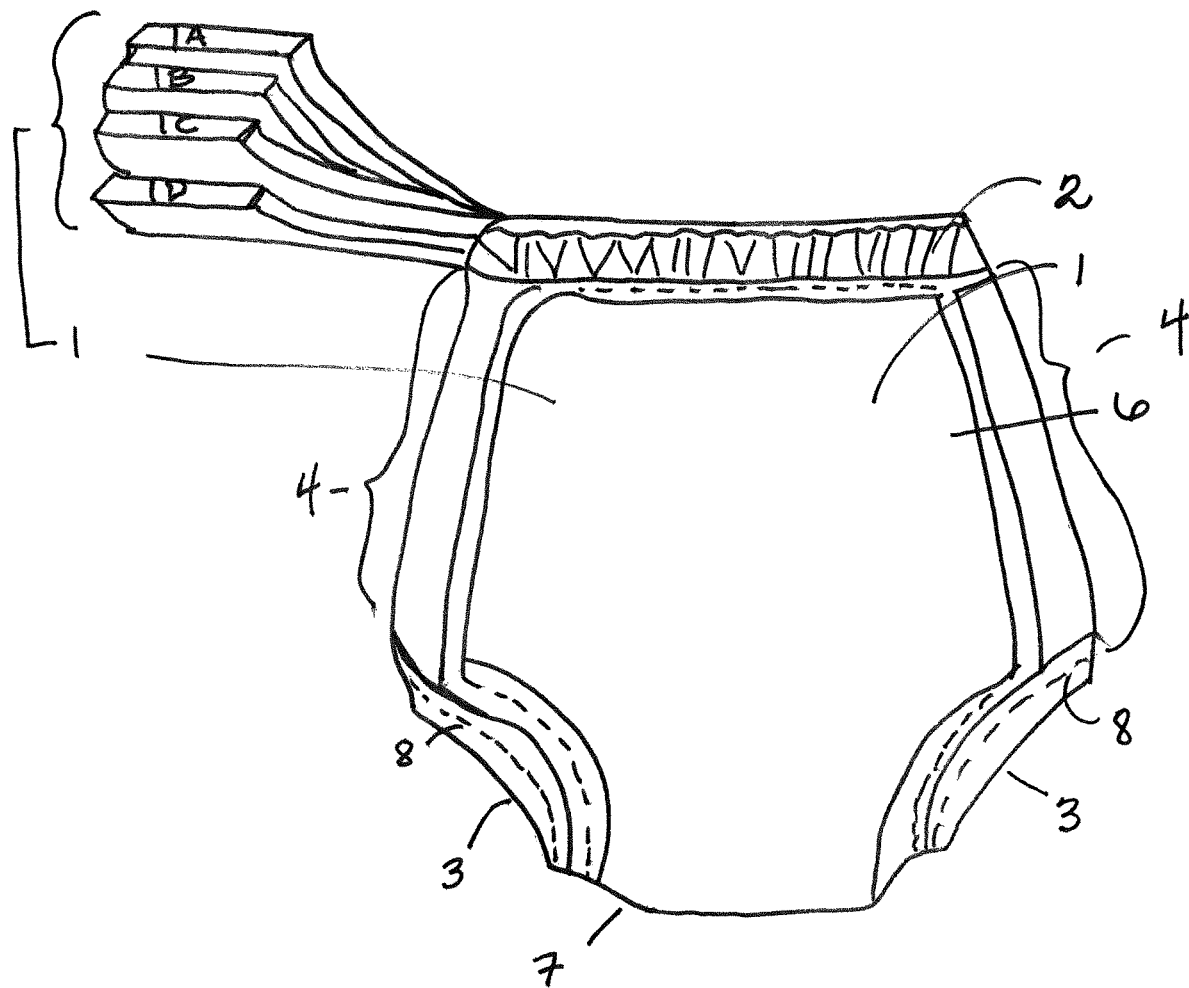
FIG. 4 is the closed rear-view of the present invention in the form of the training garment with two visible leg openings, the back panel of the garment which is inclusive of the continuous multi-layer absorbent panel nesting in the back area of the elastic waistband with the elastic waistband with an additional illustration including the exploded layers of the preferred construction of the absorbent panel. The fasteners, being fully engaged in this view and not visible showing the back panel fully connected to the front panel.

Referring now to FIG. 4, there is a full illustration of undergarment 7 from the back when fully assembled. The symmetry in the undergarment 7 is visible in this view, with the leg openings 3 laterally positioned the same as in the front view of the undergarment 7. The fasteners being nested into the sides of the front panel 5 and back panel 6, are not visible from this view but are fully engaged to show undergarment 7 in its fully assembled position. The multi-layered absorbent panel 1 layers are illustrated here as layer 1A—the outermost layer, layer 1B—the second layer from the outermost layer 1A, layer 1C—the third layer from the outermost layer 1A and layer 1D—the innermost layer and the layer next to subject-wearer's skin. Referring now to the multi-layered absorbent panel 1 illustration where the multi-layer absorbent panel 1 can have a plurality of layers within it as shown here with a preferred embodiment of four layers with at least one layer impermeable to liquid. Referring now to the one layer of the multi-layered absorbent panel 1, it is an impermeable layer, preferably layer 1B, acting as a barrier to liquid. The current invention discloses an impermeable layer 1B as a plastic or any other type of hydrophilic, water impermeable fabric. The other inner-most layers referring now to layer 1C and layer 1D of the undergarment 7 consist of highly absorbent material to facilitate an absorbency level needed for effectiveness in the undergarment 7 but not to alleviate sensory perception. In this illustration, the back panel 6 is shown with the fully integrated multi-layered absorbent panel 1 and the multi-layer absorbent panel 1 is nesting into the elastic waistband 2.

Figure 5:
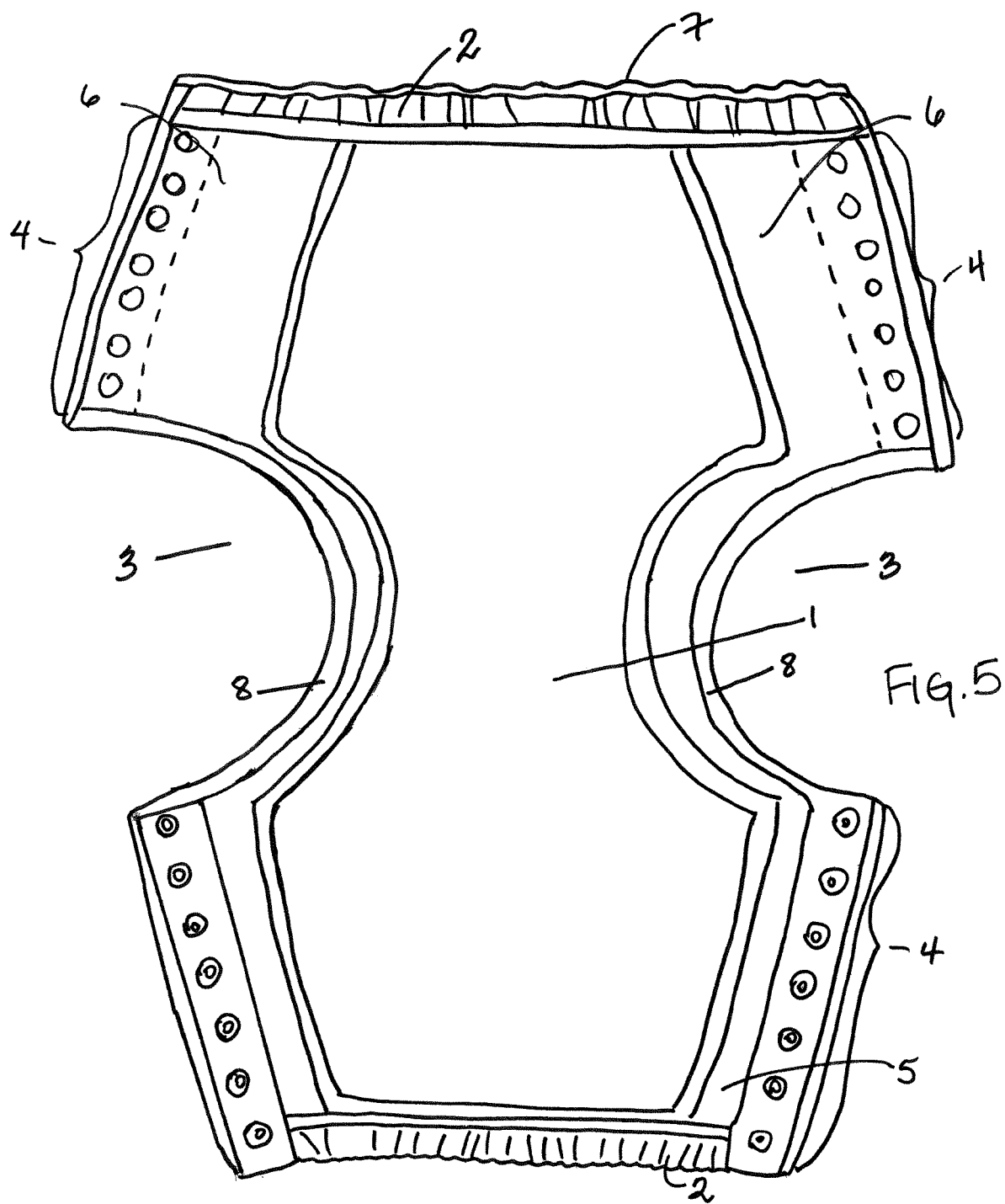
FIG. 5 is the exploded view of the present invention in the form of the training undergarment. This view exposes the inside of the training undergarment when the fasteners are not laterally engaged on either side of the garment. This view further exposes the construction of the training undergarment with the multi-layer absorbent panel in full view as it is nested in the middle of the training undergarment extending longitudinally from the front waistband region to the back waistband region nested in both the front and back waistbands. This view also exposes the relationship of the leg openings of the undergarment to the front and back panels of the training undergarment and the lateral placement of both openings to the middle panel that is the multi-layer absorbent panel when fully open. This view further exposes the plurality of fasteners to be used to close the garment to secure the garment to subject-wearer. The fasteners are affixed to both the front and back panel on lateral sides of each panel in a planned orientation to close the garment fully for secure use.

The undergarment 7 is illustrated in an exploded view now referring to FIG. 5. The view in FIG. 5 exposes the inside of the undergarment 7 and the multi-layered absorbent panel 1 as well as the inside of the front panel 5 and back panel 6 are in full view. The fasteners 4 and their lateral placement on either side of the undergarment are in full view in their vertical orientation on both the front panel 5 and the back panel 6. The location and construction of the multi-layered absorbent panel 1 is fully exposed and the construction of how the panel 1 is nested into the elastic waistband 2 on both the front panel 5 and the back panel 6. The fully integrated undergarment 7 with fasteners 4 completely unengaged above the leg openings 3 allows a completely extended undergarment 7 in this view to further expose the construction of each region of the undergarment 7.

Figure 6:
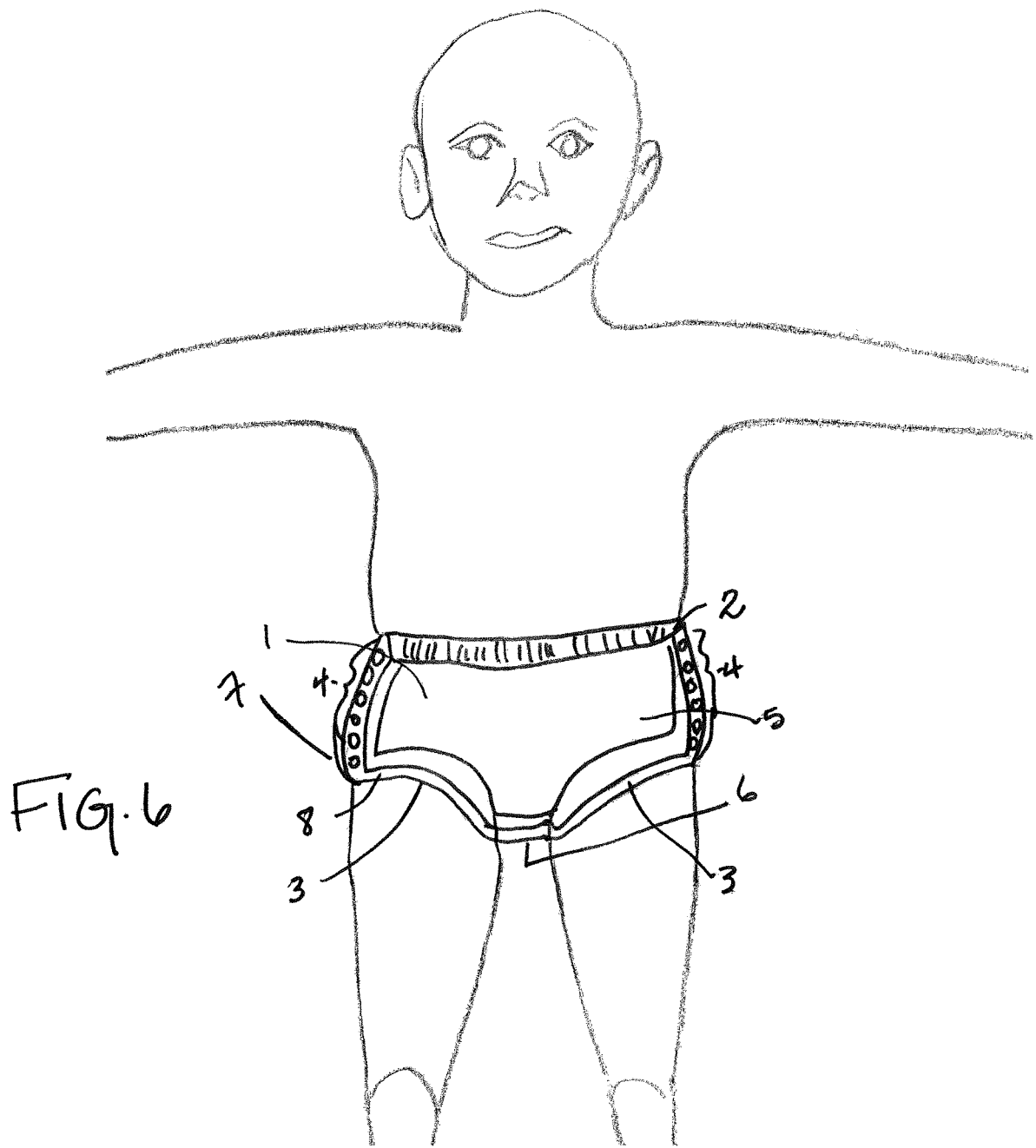
FIG. 6 is a front view of the training undergarment with the plurality of fasteners fully engaged securing the garment to a subject-wearer.

The current invention disclosed herein in its fully assembled condition can be worn over the genitals of the subject-wearer with fasteners 4 fully engaged and the undergarment 7 being donned on the subject-wearer. Now, referring to FIG. 6 the undergarment 7 is donned by subject-wearer and in this view, the fully elastic waistband 2 along with the front panel 5 and both leg openings 3 are visible as the undergarment 7 is affixed or donned on the subject-wearer. The multi-layered absorbent panel is not seen when garment is securely fastened and donned by subject-wearer.

What is claimed is:

1. A training undergarment comprising:
   an outside layer formed by a front panel and a back panel;
   an expandable, elastic waistband at a top edge of each of the front panel and back panel, wherein the elastic waistband is configured to fully encircle a wearer's waist;
   a multi-layered absorbent panel comprised of:
      an outer layer that is impermeable to liquid;
      a first inner layer, adjacent to the outermost layer, that is impermeable to liquid;
      a second inner layer, adjacent to the first inner layer, comprising a highly absorbent material; and
      an inner layer, adjacent to the second inner layer, comprising a highly absorbent material, and configured to be placed against a wearer's skin,
   wherein a first end of the multi-layered absorbent panel is nested in the elastic waistband at the top edge of the front panel, and a second end of the multi-layered absorbent panel is nested in the elastic waistband at the top edge of the back panel;
   wherein the multi-layered absorbent panel is integrated into the outside layer and is configured to prevent movement and/or bunching of the multi-layered adsorbent panel,
   wherein the training undergarment consists of organic, non-toxic, environmentally friendly materials, and
   wherein the training undergarment is configured to be washable and reusable.

2. The training undergarment of claim 1, further comprising:
   fasteners at first and second side edges of the front panel;
   mating fasteners configured to attach to said fasteners, at first and second side edges of the back panel, wherein said fasteners and said mating fasteners are configured to attach the first and second side edges of the front panel with respective first and second sides of the back panel, thereby allowing the undergarment to be simply donned and doffed without requiring a wearer to remove clothing.

3. The training undergarment of claim 1, wherein the outside layer forming the front and back panel is a single piece of textile.

4. The training undergarment of claim 2, wherein when the first and second side edges of the front panel are respectively attached to the first and second side edges of the back panel, two elastic leg openings are formed and configured to receive a wearer's legs.

5. The training undergarment of claim 2, wherein the fasteners at first and second side edges of the front panel are located on an inside of the front panel and the mating fasteners at first and second side edges of the back panel are located on an outside of the back panel, whereby an engagement of the fasteners with the mating fasteners creates a temporary but interlocking seam at the side edges of the front and back panels with a vertical orientation, thereby allowing a wearer to don the training undergarment discretely.

* * * * *